United States Patent [19]

Torihara et al.

[11] Patent Number: 5,498,799
[45] Date of Patent: Mar. 12, 1996

[54] PROCESS FOR PRODUCING OPTICALLY ACTIVE 2-NORBORNANONE

[75] Inventors: Masahiro Torihara; Yoshin Tamai, both of Niigata, Japan

[73] Assignee: Kuraray Co., Ltd., Kurashiki, Japan

[21] Appl. No.: 293,215

[22] Filed: Aug. 19, 1994

[30] Foreign Application Priority Data

Aug. 26, 1993 [JP] Japan ..................................... 5-235773
Aug. 26, 1993 [JP] Japan ..................................... 5-235775

[51] Int. Cl.$^6$ ...................................................... C07C 45/41
[52] U.S. Cl. ........................... 568/354; 549/449; 562/502
[58] Field of Search ........................... 562/502; 549/449; 568/354, 347

[56] References Cited

U.S. PATENT DOCUMENTS

| | | | |
|---|---|---|---|
| 4,007,211 | 2/1977 | Trost et al. | 568/354 |
| 4,812,476 | 3/1989 | Imwinkelried et al. | 562/579 |
| 5,214,197 | 5/1993 | Hayashi et al. | 549/449 |
| 5,266,728 | 11/1993 | Yoshida et al. | 562/502 |

FOREIGN PATENT DOCUMENTS 0528694  2/1993  European Pat. Off. .

OTHER PUBLICATIONS

Chemische Berichte, vol. 122, No. 2, Feb. 1989, Jochen Mattay, et al., "Asymmetric Induction in the Diels–Alder Reaction of Chiral (2S)-2-(tert-Butyl)5-Methylene-1,3-Dioxolan-4-One')", pp. 327–330.

Tetrahedron, vol. 49, No. 36, pp. 7871–7882, 1993, A. L. J. Beckwith, et al., "Some Diastereoselective Radical Reactions of Substituted 1.3-Dioxolan-4-Ones".

Fieser et al, "Reagents for Organic Synthesis", p. 1308 (1967).

*Primary Examiner*—James H. Reamer
*Attorney, Agent, or Firm*—Oblon, Spivak, McClelland, Maier & Neustadt

[57] ABSTRACT

An optically active 5-methylenedioxolan-4-one derivative is subjected to Diels-Alder reaction with cyclopentadiene, and the resulting Diels-Alder reaction product is hydrolyzed to convert it into an optically active 2-hydroxynorbornene-2-carboxylic acid, which is then subjected to catalytic hydrogenation to form an optically active 2-hydroxynorbornane-2-carboxylic acid. The hydroxycarboxylic acid is subjected to oxidative decarboxylation to obtain an optically active 2-norbornanone.

7 Claims, No Drawings

PROCESS FOR PRODUCING OPTICALLY ACTIVE 2-NORBORNANONE

BACKGROUND OF THE INVENTION

1. Field of the Invention

This invention relates to a process for producing an optically active 2-norbornanone useful as a starting material for synthesizing various physiologically active substances.

2. Description of the Related Art

A thromboxane A2 receptor antagonist useful as a blood coagulator can be synthesized from an optically active 3-allyl-2-norbornanone, as reported in Narisadaet al., J. Med. Chem., 31, 1847 (1988).

This optically active 3-allyl-2-norbornanone is usually produced by allylating the α-position of a carbonyl group of optically active 2-norbornanone. Hence, in the production of the thromboxane A2 receptor antagonist, it is necessary to obtain optically active 2-norbornanone.

The following three processes have been hitherto proposed as processes for producing the optically active 2-norbornanone.

A first process comprises reacting a racemic modification of endo- or exo-2-norbornanol with phthalic anhydride to form a half ester of phthalic acid, subjecting it to optical resolution by a diastereomer method, and hydrolyzing the resolution product, further followed by oxidation to obtain optically active 2-norbornanone [Winstein et al., J. Am. Chem. Soc., 74, 1147, (1952)].

A second process comprises subjecting a racemic modification of exo-2-norbornanol or 2-norbornanone to asymmetric oxidation or asymmetric reduction, respectively, using horse liver alcohol dehydrogenase to obtain optically active 2-norbornanone [Irwin et al., J. Am. Chem. Soc., 98, 8476, (1976)].

A third process comprises subjecting an optically active acrylic ester and cyclopentadiene to Diels-Alder reaction to obtain an optically active norbornene-2-carboxylic acid ester, hydrolyzing the resulting ester, and subjecting the resulting optically active norbornene-2-carboxylic acid to catalytic hydrogenation to obtain optically active norbornane-2-carboxylic acid, further followed by oxidation to convert it into optically active 2-hydroxynorbornane-2-carboxylic acid, which is finally subjected to oxidative decarboxylation to obtain optically active 2-norbornanone (Japanese Patent Application Laid-open No. 5-51345).

However, in the case of the first process, the optically active 2-norbornanone obtained can not have a sufficient optical purity. In order to improve its optical purity, complicated operations for purification such as recrystallization must be repeated, resulting in a decrease in yield of the optically active 2-norbornanone and inversely an increase in production cost. Thus, there is a problem in the industrial application of the process.

In the case of the second process, the horse liver alcohol dehydrogenase used is very expensive and also can not promise a satisfactory asymmetric yield. Thus, there is also a problem in the industrial application of the process.

In the case of the third process, optically active norbornane-2-carboxylic acid is oxidized to obtain optically active 2-hydroxynorbornane-2-carboxylic acid, where a heavy metal salt potassium permanganate is used in the oxidation and there is a possibility of adversely affecting the environment.

Moreover, this third process employs sodium bismuthate-phosphoric acid ($NaBiO_3$—$H_3PO_4$) as an oxidizing agent when the optically active 2-hydroxynorbornane-2-carboxylic acid is subjected to oxidative decarboxylation. Hence, it comes into environmental question how the heavy metal bismuth should be handled. In addition, the process can give a yield of as low as about 55%, and is not suited as an industrial means.

In this connection, regardless of an optical activity, it is proposed to carry out oxidative decarboxylation by reacting 2-hydroxynorbornane-2-carboxylic acid with an oxidizing agent, 2-chlorobenzoxazolium salt [T. Mukaiyama et al., J. Med. them. Soc., 31, 1847 (1988)] or sodium periodate [G. Helmchen et el., Tetrahadron Asymmetry, 1, 351 (1990)]. However, in order to carry out this reaction in an industrial scale, there is a problem of an excessively high material cost for the oxidizing agents. Accordingly, it is difficult to achieve industrial application of these oxidizing agents to the above third process.

Meanwhile, it is proposed to synthesize the 2-hydroxynorbornane- 2-carboxylic acid through a spironorbornanone derivative obtained by subjecting a 5-methylene-1,3-dioxolan-4-one derivative and cyclopentadiene to Diels-Alder reaction [J. Matray et al., Chem. Bar., 122, 32? (1989)].

Accordingly, it is considered possible to produce optically active 2-norbornanone through the optically active 2-hydroxynorbornane-2-carboxylic acid if the optically active 5-methylene-1,3-dioxolan-4-one derivative can be simply produced.

Incidentally, regardless of an optical activity, it is proposed to produce a 5-methylene-1,3-dioxolan-4-one derivative by reacting a 5-bromo-5-methyl-1,3-dioxolan-4-one derivative with a dehydrohalogenating agent such as triethylamine [J. Matray et al., Chem. Bar., 122, 327 (1989)] or 1,8-diazabicyclo[5,4,0]-undeca-7-ene (DBU) [D. Seebach et al., Helv. Chim. Acta., 79, 1104 (1987)]. It is also proposed to produce it by reacting a 5-phenylsulfonylmethyl- 1,3-dioxolan-4-one derivative with DBU [W. R. Rouch et al., J. Org. Chem., 57, 3380 (1992)].

However, there are the problems that the yield is as low as about 60% when triethylamine is used and in the meantime the DBU is expensive. There is another problem that the 5-phenylsulfonylmethyl derivative itself requires a high production cost. Thus, it is difficult from an industrial viewpoint to apply the production of 5-methylene- 1,3-dioxolan-4-one derivative by the use of triethylamine or DBU as a dehydrohalogenating agent to the production of optically active 2-norbornanone.

SUMMARY OF THE INVENTION

This invention intends to solve the problems involved in the prior art discussed above, and an object thereof is to make it possible to simply produce in an industrial scale the optically active 2-norbornanone useful as a starting material for synthesizing various physiologically active substances including the thromboxane A2 receptor antagonist useful as a blood coagulator.

Another object of the present invention is to make it possible to produce in an industrially advantageous manner the 2-hydroxynorbornene-2-carboxylic acid, a starting material for synthesizing optically active 2-norbornanone.

Still another object of the present invention is to make it possible to obtain 2-norbornanone by subjecting 2-hydroxynorbornane-2-carboxylic acid to oxidative decarboxylation in an industrially advantageous manner.

A further object of the present invention is to make it possible to obtain a 5-methylene-1,3-dioxolan-4-one derivative by subjecting a 5-halogeno-5-methyl-1,3-dioxolan-4-one derivative to dehydrohalogenation in an industrially advantageous manner.

The present invention provides a process for producing an optically active 2-norbornanone represented by Formula (1a) or (1b):

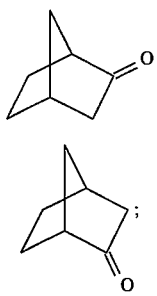

said process comprising the steps of;

a. allowing an optically active dioxolan-4-one derivative represented by Formula (2*)

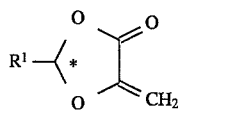

wherein R represents a substituted or unsubstituted alkyl group or aryl group, and * represents an asymmetric carbon atom;
to react with cyclopentadiene to form a compound represented by Formula (3a) or (3b):

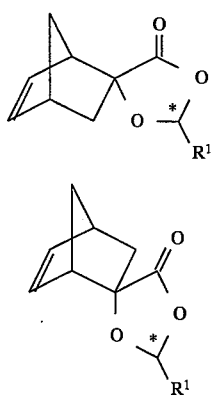

wherein $R^1$ and * are as defined in Formula (2*);

b. hydrolyzing the compound of Formula (3a) or (3b) obtained in the step a., to convert it into an optically active 2-hydroxynorbornene-2-carboxylic acid represented by Formula (4a) or (4b):

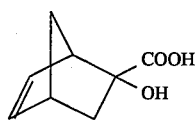

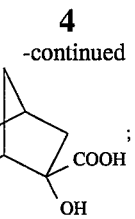

c. subjecting the compound of Formula (4a) or (4b) obtained in the step b., to catalytic hydrogenation to form a compound represented by Formula (5a) or (5b):

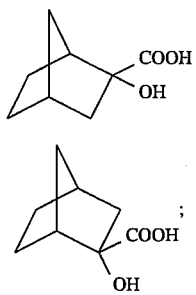

d. subjecting the compound of Formula (5a) or (5b) obtained in the step c., to oxidative decarboxylation to form the optically active 2-norbornanone of Formula (1a) or (1b).

The present invention also provides a process for producing an optically active 2-hydroxynorbornene-2-carboxylic acid represented by Formula (4a) or (4b):

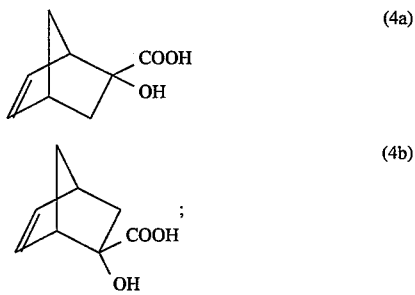

said process comprising the steps of;

a. allowing an optically active dioxolan-4-one derivative represented by Formula (2*)

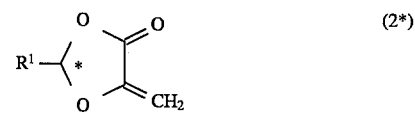

wherein $R^1$ represents a substituted or unsubstituted alkyl group or aryl group, and * represents an asymmetric carbon atom;
to react with cyclopentadiene to form a compound represented by Formula (3a) or (3b):

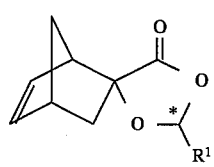

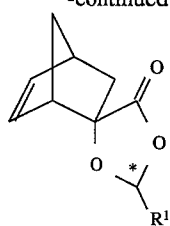
(3b)

wherein $R^1$ and * are as defined in Formula (2*);

b. hydrolyzing the compound of Formula (3a) or (3b) obtained in the step a., to convert it into the optically active 2-hydroxynorbornene-2-carboxylic acid of Formula (4a) or (4b).

The present invention still also provides a process for producing 2-norbornanone represented by Formula (1):

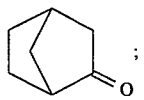
(1)

said process comprising the step of subjecting 2-hydroxynorbornane- 2-carboxylic acid represented by Formula (5):

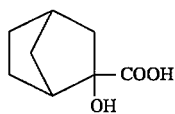
(5)

to oxidative decarboxylation in the presence of a hypohalogenite to obtain the 2-norbornanone of Formula (1).

The present invention further provides a process for producing a 5-methylene-1,3-dioxolan-4-one represented by Formula (2):

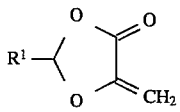
(2)

wherein $R^1$ represents a substituted or unsubstituted alkyl group or aryl group;

said process comprising the step of allowing a 5-halogeno- 5-methyl-1,3-dioxolan-4-one derivative represented by Formula (6):

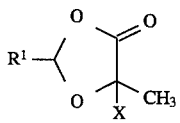
(6)

wherein $R^1$ is as defined in Formula (2), and X represents a halogen atom;

to react with a tertiary amine represented by Formula (7):

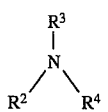
(7)

wherein $R^2$ $R^3$ and $R^4$ each independently represent an alkyl group having 4 to 12 carbon atoms; to convert said derivative into the compound of Formula (2).

DETAILED DESCRIPTION OF THE INVENTION

The process for producing optically active 2-norbornanone according to the present invention will be first described below with reference to the following scheme.

Scheme 1

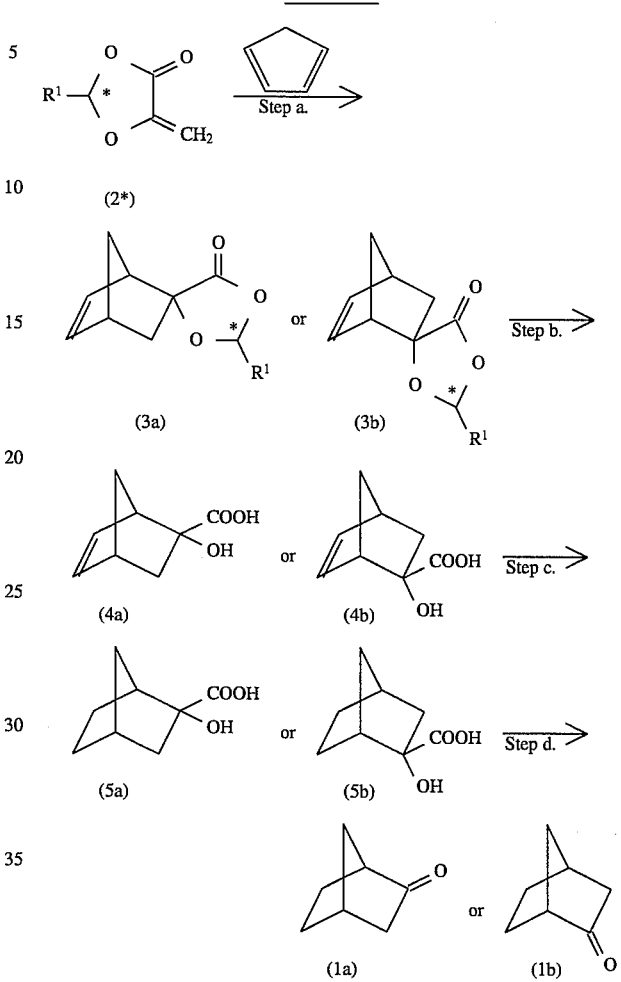

In the compounds shown in Scheme 1, $R^1$ represents a substituted or unsubstituted alkyl group such as methyl, ethyl, tert-butyl, cyclohexyl or benzyl, or a substituted or unsubstituted aryl group such as phenyl, toluyl, naphthyl or furanyl; and * represents an asymmetric carbon atom.

Step a

In the present invention, the optically active dioxolan-4-one derivative of Formula (2*) is first subjected to Diels-Alder reaction with cyclopendadiene to form a spiro compound of Formula (3a) or (3b). In this step, when the absolute configuration about the asymmetric carbon atom of the compound of Formula (2*) is 2S, the compound of Formula (3a) is stereoselectively produced. When it is inversely 2R, the compound of Formula (3b) is stereoselectively produced.

This Diels-Alder reaction can be carried out by stirring a mixture comprised of the optically active dioxolan-4-one derivative of Formula (2*) and cyclopentadiene, usually at a temperature of from room temperature to 100° C., whereby the spiro compound of Formula (3a) or (3b) can be quantitatively formed. In this case, the cyclopentadiene may preferably be used in an amount of from 1.5 to 5.0 mols per mol of the optically active dioxolan-4-one derivative of Formula (2*).

No solvent may be used when the Diels-Alder reaction is carried out. If necessary, a solvent that does not adversely affect the reaction may be used, as exemplified by aromatic hydrocarbons such as benzene and toluene, aliphatic hydrocarbons such as pentane, hexane and heptane, ethers such as tetrahydrofuran and diethyl ether, and aliphatic halides such as dichloromethane, chloroform and dichloroethane.

The starting optically active dioxolan-4-one derivative of Formula (2*) can be obtained by various methods. For example, when $R^1$ is tert-butyl, it can be readily produced from a reaction product of pivalic aldehyde with L-(−)- or L-(+)-lactic acid [J. Matray et al., Chem. Bet., 122,327 (1989)]; J. Org. Chem., 57, 3380 (1992)].

Step b

Next, the optically active spiro compound of Formula (3a) or (3b) is hydrolyzed to convert it into an optically active 2-hydroxynorbornene-2-carboxylic acid represented by Formula (4a) or (4b).

The hydrolysis may preferably be carried out under basic conditions. For example, it can be carried out by stirring the spiro compound of Formula (3a) or (3b) in an aqueous solution of an alkali metal hydroxide such as lithium hydroxide, sodium hydroxide or potassium hydroxide, an alkaline earth metal hydroxide such as calcium hydroxide or magnesium hydroxide or an alkali metal carbonate such as sodium carbonate or potassium carbonate. This hydrolysis gives an optically active 2-hydroxynorbornene- 2-carboxylate dissolved in an aqueous reaction solution.

When the hydrolysis is carried out, an organic solvent may be added to the reaction solution in order to improve the rate of hydrolysis of the spiro compound of Formula (3a) or (3b). When an organic solvent miscible with water is used, the reaction proceeds in a uniform system, and when an organic solvent immiscible with water is used, the reaction proceeds in a two-phase system. In view of the rate of hydrolysis, the safety and the handling, it is preferable to add a lower alcohol such as methanol, ethanol or propanol. Reaction temperature and reaction time may be appropriately selected.

Next, from the hydrolysis reaction solution in which the optically active 2-hydroxynorbornene-2-carboxylate is dissolved, the organic solvent such as a lower alcohol is optionally removed by evaporation, and water and an extraction solvent such as hexane are further added to the residue so that the water-insoluble components are removed by their extraction to the hexane phase. Then, the aqueous phase in which the 2-hydroxynorbornene-2-carboxylate is dissolved is made acidic using a mineral acid such as sulfuric acid to adjust its pH preferably to 1 to 2 to convert the compound into 2-hydroxynorbornene-2-carboxylic acid of Formula (4a) or (4b). Next, the resulting carboxylic acid is extracted with an extraction solvent such as isopropyl ether, followed by removal of the extraction solvent by a conventional method, so that the 2-hydroxynorbornene-2-carboxylic acid of Formula (4a) or (4b) can be isolated. This compound can be used as a starting material for the next step as it is crude, or may be purified by recrystallization since it has a good crystallizability.

Step c

Next, the optically active 2-hydroxynorbornene-2-carboxylic acid of Formula (4a) or (4b) is subjected to catalytic hydrogenation to reduce it to respectively corresponding optically active 2-hydroxynorbornane-2-carboxylic acid represented by Formula (5a) or (5b).

The catalytic hydrogenation can be carried out by dissolving the optically active 2-hydroxynorbornene-2-carboxylic acid of Formula (4a) or (4b) in a solvent including lower alcohols such as methanol, ethanol and propanol, esters such as ethyl acetate, propyl acetate and butyl acetate and hydrocarbons such as pentane, hexane and heptane, and adding to the resulting solution a catalytic hydrogenation catalyst such as palladium-carbon, followed by stirring usually in an atmosphere of hydrogen gas of 1 kg/cm² to 50 kg/cm² at a temperature of from room temperature to 100° C.

After the catalytic hydrogenation has been completed, the catalyst for catalytic hydrogenation is separated by filtration and the filtrate is condensed, whereby the optically active 2-hydroxynorbornane-2-carboxylic acid of Formula (5a) or (5b) can be obtained.

Step d

Next, the optically active 2-hydroxynorbornane-2-carboxylic acid of Formula (5a) or (5b) is subjected to oxidative decarboxylation to form respectively corresponding optically active 2-norbornanone of Formula (1a) or (1b).

The oxidative decarboxylation can be carried out by reacting the carboxylic acid of Formula (5a) or (5b) with an oxidizing agent such as hypohalogenite (a salt of hypohalorous acid) or lead tetraacetate, chromic acid-sulfuric acid or sodium bismuthate-phosphoric acid by a conventional method. Of these, hypohalogenite may preferably be used, since it is readily available, low in cost and contains no heavy metal. In particular, sodium hypochlorite may preferably be used.

The oxidative decarboxylation may be carried out under conditions appropriately set in accordance with the type of the oxidizing agent used. For example, when sodium hypochlorite is used as the oxidizing agent, it can be carried out by dropwise adding an aqueous solution of sodium hypochlorite to the carboxylic acid of Formula (5a) or (5b) with stirring, at a temperature of from −10° C. to 40° C.

After the decarboxylation has been completed, the 2-norbornanone of Formula (1a) or (1b) is extracted from the reaction solution with an extraction solvent such as hexane, and its organic phase is washed by a conventional method and then dried, followed by removal of the extraction solvent, so that the optically active 2-norbornanone of Formula (1a) or (1b) can be obtained. This compound can be purified by distillation under reduced pressure or by recrystallization.

In a series of reaction of Scheme 1 described above, the optically active dioxolan-4-one derivative of Formula (2*) has a double bond conjugated with α-carbonyl, and hence can readily undergo the Diels-Alder reaction with cyclopentadiene. The optically active spiro compound obtained by this Diels-Alder reaction can be readily hydrolyzed to the optically active 2-hydroxynorbornene-2-carboxylic acid serving as the starting material for producing the optically active 2-norbornanone. The optically active dioxolan-4-one derivative is also a readily available compound. Thus, the optically active 2-norbornanone can be produced according to the Scheme 1 in an industrially advantageous manner.

In the above process for producing the optically active 2-norbornanone, the reaction in Step d. proceeding from the 2-hydroxynorbornane-2-carboxylic acid to the optically active 2-norbornanone is important as a process commonly used to produce 2-norbornanone without regard to whether it is optically active or not, that utilizes oxidative decarboxylation of 2-hydroxynorbornane-2-carboxylic acid.

More specifically, as described above, the 2-norbornanone can be produced by reacting 2-hydroxynorbornane-2-carboxylic acid with an oxidizing agent of various types. It can be more preferably produced by its reaction with a hypohalogenite as shown in Scheme 2 below. This enables oxidative decarboxylation of 2-hydroxynorbornane-2-carboxylic acid in a very good efficiency. In addition, the hypohalogenite, including sodium hypochlorite, is very inexpensive.

Hence, the process in which the 2-hydroxynorbornane-2-carboxylic acid is subjected to oxidative decarboxylation by the action of the hypohalogenite can be very useful. In particular, when an optically active compound is used as the 2-hydroxynorbornane-2-carboxylic acid, the compound by no means lacemizes before and after the oxidative decarboxylation as described in Step c. of Scheme 1. Therefore, the process of producing 2-norbornanone according to Scheme 2 is suitable when the optically active 2-norbornanone is produced.

Scheme 2

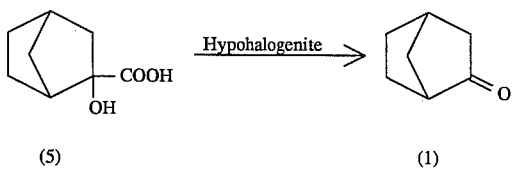

(5)         (1)

In the process for producing 2-norbornanone according to this Scheme 2, alkali metal salts of hypochlorous acid, hypobromous acid or hypoiodous acid may preferably be used as the hypohalogenite. In particular, sodium hypochlorite, which is readily available, inexpensive and also contains no heavy metal, may particularly preferably be used.

The oxidative decarboxylation may be carried out under conditions appropriately set in accordance with the type of the hypohalogenite used. For example, when sodium hypochlorite is used as the oxidizing agent, the oxidative decarboxylation can be carried out by mixing and stirring 2-hydroxynorbornane-2-carboxylic acid and sodium hypochlorite at a temperature of from −10° C. to 40° C., and preferably from 0° to 20° C.

The sodium hypochlorite may preferably be used in an amount of from 1.00 to 1.50 equivalent weight, and more preferably from 1.05 to 1.10 equivalent weight, based on the weight of 2-hydroxynorbornane-2-carboxylic acid.

Usually, as the sodium hypochlorite, those commercially available in the form of a 12% aqueous solution may preferably be used.

No solvent may be used when this oxidative decarboxylation is carried out. If necessary, water or a two-phase type reaction solvent comprised of water and an aromatic hydrocarbon such as benzene or toluene or an aliphatic hydrocarbon such as pentane, hexane or heptane may be used. When the oxidative decarboxylation is carried out, a mineral acid such as hydrochloric acid,.an organic acid such as acetic acid or an acetic acid type buffer may also be optionally added.

After the reaction has been completed, the 2-norbornanone can be obtained from the reaction solution by a conventional method. For example, the reaction solution is extracted with a solvent such as hexane, and the organic layer thus formed is successively washed with an aqueous sodium thiosulfate solution, a saturated aqueous sodium hydrogencarbonate solution and a saturated brine, followed by evaporation of the solvent under reduced pressure and then distillation of the resulting residue under reduced pressure, so that the 2-norbornanone can be obtained.

In the process for producing 2-norbornanone according to this Scheme 2, the 2-hydroxynorbornane-2-carboxylic acid of Formula (5) is by no means limited to the compound produced in the course of Scheme 1, and can be obtained by various methods. For example, those produced by the method disclosed in Japanese Patent Application Laid-open No. 5-51345 and so forth can be used.

Incidentally, the optically active 5-methylene-1,3-dioxolan-4-one derivative of Formula (2*), the starting material for the reaction of Scheme 1, can be obtained by dehydrohalogenation of the corresponding optically active 5-halogeno-5-methyl-1,3-dioxolan-4-one derivative. This dehydrohalogenation itself is important as a process commonly used to produce 5-methylene-1,3-dioxolan-4-one derivative without regard to whether it is optically active or not, that utilizes dehydrohalogenation of a 5-halogeno- 5-methyl-1, 3-dioxolan-4-one derivative.

More specifically, as shown in Scheme 3, the 5-methylene- 1,3-dioxolan-4-one derivative of Formula (2) can be more preferably produced by reacting a 5-halogeno-5-methyl- 1,3-dioxolan-4-one derivative of Formula (6) with a tertiary amine of Formula (7).

Scheme 3

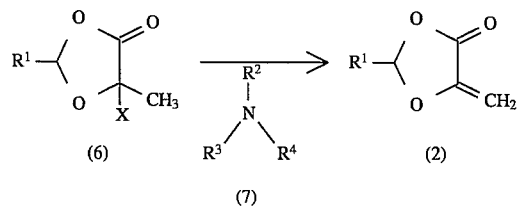

In the compounds of Scheme 3, $R^1$ is as defined in Formula (2*), X represents a halogen atom such as chlorine or bromine, and $R^2$ $R^3$ and $R^4$ each independently represent an alkyl group having 4 to 12 carbon atoms.

In this process for producing the 5-methylene-1,3-dioxolan- 4-one derivative, specifically stated, the dehydrohalogenation can be carried out by heating and stirring a mixture of the 5-halogeno-5-methyl-dioxolan-4-one derivative of Formula (6) and the tertiary amine of Formula (7) at a temperature ranging preferably from room temperature to 150° C., and more preferably from 50° to 100° C. In this case, the tertiary amine of Formula (? ) may preferably be used in an amount of from 1.0 to 10.0 equivalent weight, and more preferably from 1.0 to 1.5 equivalent weight, based on the weight of the 5-halogeno-5-methyl-dioxolan- 4-one derivative of Formula (6).

As the tertiary amine of Formula (7), those substituted with an alkyl group having 4 to 12, and preferably 8 to 10, carbon atoms must be used. This is because use of those substituted with an alkyl group having less than 4 or more than 12 carbon atoms may result in a decrease in yield of the dehydrohalogenation. Here, the alkyl groups $R^2$, $R^3$ and $R^4$ in the tertiary amine of Formula (7) may be straight-chain, branched or cyclic, and can be exemplified by a butyl group, an isobutyl group, a hexyl group, a cyclohexyl group, a 2-ethylhexyl group and an octyl group. The alkyl groups $R^2$, $R^3$ and $R^4$ may also be the same or different from one another.

In the reaction of Scheme 3, no solvent may be used when the dehydrohalogenation is carried out. If necessary, a solvent that does not adversely affect the reaction may be used, as exemplified by aromatic hydrocarbons such as benzene and toluene, aliphatic hydrocarbons such as pentane, hexane and heptane, ethers such as tetrahydrofuran and diethyl ether, and aliphatic halides such as dichloromethane, chloroform, carbon tetrachloride and dichloroethane.

After the dehydrohalogenation has been completed, the intended 5-methylene-1,3-dioxolan-4-one derivatives can be isolated from the reaction solution by a conventional method. For example, the reaction solution is washed with water and thereafter the solvent is removed from its organic layer under reduced pressure, followed by distillation of the resulting residue under reduced pressure, so that the 5-methylene-1,3-dioxolan-4-one derivatives can be obtained.

The starting 5-halogeno-5-methyl-1,3-dioxolan-4-one derivative of Formula (6) in this production process can be produced by various methods. For example, it can be produced by the method disclosed in J. Matray et al., them. Bet., 122, 327 (1989).

As described above, in the process of Scheme 3, when 5-halogeno-5-methyl-1,3-dioxolan-4-ones are reacted with a dehydrohalogenating agent to convert them into 5-methylene-1,3-dioxolan-4-ones, the tertiary amine substituted with an alkyl group having its carbon atom number within the specific range is used as the dehydrohalogenating agent. This makes it possible to carry out dehydrohalogenation in a good yield. In addition, such a tertiary amine is readily available and inexpensive. Hence, the dehydrohalogenation can be readily applied in an industrial scale and therefore the production cost of end products can be cut down.

EXAMPLES

The process for producing the optically active dioxolan-4-one derivative serving as the starting material in the production process of Scheme 1 will be further described below as a reference example, and also the respective schemes will be specifically described by giving Examples.

Reference Example

Synthesis of
(2S)-2-tert-butyl-5-methylene-1,3-dioxolan- 4-one
of Formula (2*)

Step 1

To a pentane solution of 86.0 g of pivalic aldehyde, 45.0 g of L-(−)-lactic acid, 1.0 g of p-toluenesulfonic acid monohydrate and two drops of sulfuric acid were added. This reaction solution was heated, and refluxed for 10 hours while removing the water formed. After the reaction was completed, the reaction solution was washed with a saturated aqueous sodium hydrogencarbonate solution and subsequently with a saturated brine, and thereafter the pentane was removed from the reaction solution. The resulting evaporation residue was recrystallized from hexane to obtain 48.0 g of (2S,5S)-2-tert-butyl-5-methyl- 1,3-dioxolan-4-one.

Step 2

In 500 ml of carbon tetrachloride, 48.0 g of the (2S,5S)-2-tert-butyl-5-methyl-1,3-dioxolan-4-one obtained in Step 1 was dissolved. To the resulting solution, 54.0 g of N-bromosuccinimide and 1.0 ml of benzoyl peroxide were added, and the solution was refluxed for 2 hours. After the reaction solution was left to have cooled, insolubles were separated by filtration and the filtrate was successively washed with an aqueous 10% sodium thiosulfate solution, a saturated aqueous sodium hydrogencarbonate solution and a saturated brine. From the filtrate thus washed, the carbon tetrachloride was evaporated under reduced pressure, and the resulting residue was recrystallized from hexane to obtain 70.5 g of (2S,5S)-5-bromo-2-tert-butyl-5-methyl-1,3-dioxolan-4-one.

Step 3

In 500 ml of carbon tetrachloride, 50.5 g of the (2S,5S)-5-bromo-2-tert-butyl-5-methyl-1,3-dioxolan-4-one obtained in Step 2 was dissolved. To the resulting solution, 50.0 g of triethylamine was added, and the solution was refluxed for 4 hours. After the reaction solution was left to have cooled, insolubles were separated by filtration, the carbon tetrachloride was evaporated under reduced pressure, and the resulting residue was recrystallized from hexane to obtain 29.5 g of (2S)-2-tert-butyl-5-methylene-1,3-dioxolan-4-one.

Data of physical properties of this compound are shown below.

Boiling point: 59.0°–61.5° C./6 Torr

Specific rotation $[\alpha]^{25}D$: −14.8° (c=1.51, CHCl$_3$)

$^1$H-NMR (300 MHz, CDCl$_3$, δ): 0.97 (9H, s), 4.85 (1H, d, J= 2.7 Hz), 5.12 (1H, d, J =2.7 Hz, 5.45 (1H, s).

$^{13}$C-NMR (75.5 MHz, CDCl$_3$, δ): 24.4, 37.5, 92.6, 111.1, 146.0, 162.6

Example 1

Synthesis of (+)-2-norbornanone of Formula (1a)

Step a 15.6 g of the (2S)-2-tert-butyl-5-methylene-1,3-dioxolan-4-one of Formula (2*) obtained in Reference Example and 30.0 g of cyclopentadiene were put in a sealed tube to carry out Dials-Alder reaction at room temperature (20° to 25° C.) for 48 hours. After the reaction was completed, unreacted cyclopentadiene was evaporated from the reaction mixture under reduced pressure to obtain 46.0 g of a crude spiro compound of Formula (3a).

Step b

To 46.0 g of the crude spiro compound obtained in Step a., 100 ml of methanol, 10 ml of water and 6.0 g of sodium hydroxide were added, and the resulting mixture was stirred for 1 hour to carry out hydrolysis. After the reaction was completed, the methanol was evaporated from the reaction mixture under reduced pressure. To the resulting residue, 100 ml of water was added, which was then washed twice with 100 ml of hexane. To the aqueous phase thus washed, sulfuric acid was added to adjust its pH to 1 to 2, followed by extraction with 100 ml of isopropyl ether, which was operated twice. From the resulting isopropyl-ether extract, the isopropyl ether was evaporated under reduced pressure, and the resulting residue was recrystallized from isopropyl ether to obtain 13.8 g of 2-hydroxy-5-norbornene-2-carboxylic acid of Formula (4a) in the form of opaque white crystals. Its yield from the (2S)-2-tert-butyl-5-methylene-1, 3-dioxolan- 4-one of Formula (2) was 90%.

Step c

In 100 ml of ethyl acetate, 10.0 g of the 2-hydroxy-5-norbornene-2-carboxylic acid of Formula (4a) obtained in Step b. was dissolved. To the resulting solution, 0.5 g of 10% palladium carbon was further added as a catalyst for catalytic hydrogenation. This solution was stirred for 2 hours in an atmosphere of hydrogen gas to carry out catalytic hydrogenation. After the reaction was completed, the catalyst was separated by filtration and the ethyl acetate was evaporated from the filtrate under reduced pressure to obtain 14.5 g of crude 2-hydroxynorbornane- 2-carboxylic acid of Formula (5a).

Step d

While stirring 14.5 g of the crude 2-hydroxynorbornane-2-carboxylic acid of Formula (5a) obtained in Step c., 50.0 g of an aqueous 12% sodium hypochlorite solution was slowly dropwise added thereto to carry out oxidative decarboxylation for 1 hour. In the course of the react-ion, the reaction solution was kept at 10° to 15° C. by ice-cooling. After the reaction was completed, the reaction solution was extracted with hexane, and the resulting organic layer was successively washed with an aqueous 10% sodium thiosulfate solution, a saturated aqueous sodium hydrogencarbonate solution and a saturated brine. From the organic layer thus washed, the hexane was evaporated under reduced pressure, and the resulting residue was distilled under reduced pressure to obtain 6.5 g of optically active (+)-2-norbornanone of Formula (1a). Its total yield from the starting (2S)-2-tert-butyl- 5-methylene-1,3-dioxolan-4-one of Formula (2*) was 82%.

Data of physical properties Of this compound are shown below.

Melting point: 96°–97° C.

Specific rotation $[\alpha]^{25}D$: +27.5 (c =1.51, $CHCl_3$)

$^1$H-NMR (300 MHz, $CDCl_3$, δ): 1.38–1.60 (3H, m), 1.70–1.90 (4H, m), 2.50–2.11 (1H, m) 2.59 (1H, br. s), 2.67 (1H, br. s)

$^{13}$C-NMR (75.5 MHz, $CDCl_3$, δ): 24.1, 27.1, 35.2, 37.6, 45.2, 49.8, 218.2

Example 2

While stirring 15.6 g of 2-hydroxynorbornane-2-carboxylic acid kept at 10° to 15° C. by ice-cooling, 65.1 g of an aqueous 12% sodium hypochlorite solution was slowly dropwise added thereto. After the addition was completed, the reaction solution was stirred at 10° to 15° C. for 1 hour to age the reaction. After the reaction was completed, the reaction solution was extracted with hexane, and the resulting organic layer was successively washed with an aqueous 10% sodium thiosulfate solution, a saturated aqueous sodium hydrogencarbonate solution and a saturated brine. From the organic layer thus washed, the hexane was evaporated under reduced pressure, and the resulting residue was distilled under reduced pressure to obtain 10.3 g of 2-norbornanone (yield: 93%).

Data of physical properties of the 2-norbornanone thus obtained are shown below.

Melting point: 95°–97° C.

$^1$H-NMR (300 MHz, $CDCl_3$, δ): 1.38–1.60 (3H, m), 1.70–1.90 (4H, m), 2.50–2.11 (1H, m), 2.59 (1H, br. s), 2.67 (1H, br. s)

$^{13}$C-NMR (75.5 MHz, $CDCl_3$, δ): 24.1, 27.1, 35.2, 37.6, 45.2, 49.8, 218.2

Example 3

In 100 ml of water, 15.6 g of 2-hydroxynorbornane-2-carboxylic acid was dissolved. To the resulting solution, 100 ml of hexane was added to form a two-phase reaction solution. To this reaction solution, 65.1 g of an aqueous 12% sodium hypochlorite solution was slowly dropwise added. After the addition was completed, the reaction solution was stirred at 10° to 15° C. for 1 hour to age the reaction. After the reaction was completed, the aqueous phase was removed from the reaction solution, and the organic layer was successively washed with an aqueous 10% sodium thiosulfate solution, a saturated aqueous sodium hydrogencarbonate solution and a saturated brine. From the organic layer thus washed, the hexane was evaporated under reduced pressure, and the resulting residue was distilled under reduced pressure to obtain 9.9 g of 2-norbornanone (yield: 90%).

Example 4

In an acetic acid buffer (pH: 5.0), 15.6 g of 2-hydroxynorbornane- 2-carboxylic acid was dissolved. The solution was kept at 10° to 150° C. by ice-cooling. While stirring it, 65.1 g of an aqueous 12% sodium hypochlorite solution was slowly dropwise added. After the addition was completed, the reaction solution was stirred at 10° to 15° C. for 1 hour to age the reaction. After the reaction was completed, the reaction solution was extracted with hexane, and the resulting organic layer was successively washed with an aqueous 10% sodium thiosulfate solution, a saturated aqueous sodium hydrogencarbonate solution and a saturated brine. From the organic layer thus washed, the hexane was evaporated under reduced pressure, and the resulting residue was distilled under reduced pressure to obtain 8.8 G of 2-norbornanone (yield: 80%).

Example 5

In 50 ml of cyclohexane, 2.37 g of 2-tert-butyl-5-bromo-5-methyl-1,3-dioxolan-4-one was dissolved. To this solution, 0.50 g of n-decane (an internal standard substance for gas chromatographic analysis) and 3.89 g of trioctylamine were added, and the solution was refluxed for 2 hours to carry out dehydrohalogenation. The reaction solution was analyzed by gas chromatography to ascertain that 2-tert-butyl-5-methylene-1,3-dioxolan-4-one was formed in a conversion of 100% and a yield of 93%.

The reaction solution was left to have cooled and thereafter successively washed with water, a saturated aqueous sodium hydrogencarbonate solution and a saturated brine. The solvent cyclohexane was evaporated under reduced pressure, and the resulting residue was distilled under reduced pressure to obtain 1.33 9 of the intended 2-tert-butyl- 5-methylene-1,3-dioxolan-4-one (isolation yield: 85%).

Data of physical properties of this compound are shown below.

Boiling point: 59.0°–61.5° C./6 Torr $^1$H-NMR (300 MHz, $CDCl_3$, δ): 0.97 (9H, s), 4.85 (1H, d, J= 2.7 Hz), 5.12 (1H, d, J =2.7 Hz, 5.43 (1H, s) $^{13}$C-NMR (75.5 MHz, $CDCl_3$, δ): 24.4, 37.5, 92.6, 111.1, 146.0, 162.6

Example 6

Example 5 was repeated to carry out dehydrohalogenation, except that the cyclohexane was replaced with carbon tetrachloride. As a result, it was ascertained that, in a reaction time of I hour, 2-tert-butyl- 5-methylene-1,3-dioxolan-4-one was formed in a conversion of 100% and a yield of 90%.

Example 7

Example 5 was repeated to carry out dehydrohalogenation, except that the trioctylamine was replaced with 2.04 g of tributylamine. As a result, it was ascertained that, in a reaction time of 2 hours, 2-tert-butyl- 5-methylene-1,3-dioxolan-4-one was formed in a conversion of 100% and a yield of 77%.

Example 8

Example 5 was repeated to carry out dehydrohalogenation, except that the cyclohexane was replaced with heptane and the trioctylamine was replaced with 2.04 g of tributylamine. As a result, it was ascertained that, in a reaction time of 1 hour, 2-tert-butyl- 5-methylene-1,3-dioxolan-4-one was formed in a conversion of 100% and a yield of 78%.

Comparative Example 1

Example 5 was repeated to carry out dehydrohalogenation, except that the trioctylamine was replaced with 5.06 g of triethylamine. As a result, even though the reaction time was extended to 6 hours, the conversion was 92%, not reaching 100%, and the 2-tert-butyl- 5-methylene-1,3-dioxolan-4-one was in a yield of as low as 53%.

Comparative Example 2

Example 5 was repeated to carry out dehydrohalogenation, except that the trioctylamine was replaced with 7.16 g of tripropylamine. As a result, even though the reaction time was extended to 6 hours, the conversion was 80%, not reaching 100%, and the 2-tert-butyl- 5-methylene-1,3-dioxolan-4-one was in a yield of as low as 38%.

What is claimed is:

1. A process for producing an optically active 2-norbornanone represented by Formula (1a) or (1b):

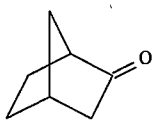
(1a)

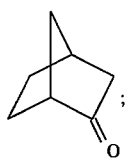
(1b)

said process comprising the steps of;

a) allowing an optically active dioxolan-4-one derivative represented by the Formula (2*)

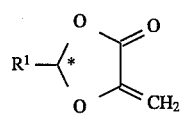
(2*)

wherein $R^1$ represents a substituted or unsubstituted alkyl group or aryl group, and * represents an asymmetric carbon atom; to react with cyclopentadiene to form a compound represented by formula (3a) or (3b):

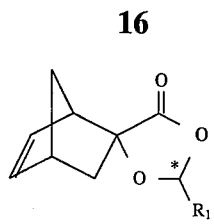
(3a)

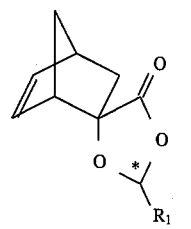
(3b)

wherein $R^1$ and * are as defined in Formula (2*);

b) hydrolyzing the compound of Formula (3a) or (3b) obtained in the step a), to convert it into an optically active 2-hydroxynorbornene-2-carboxylic acid represented by Formula (4a) or (4b):

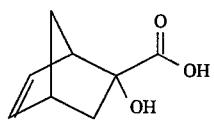
(4a)

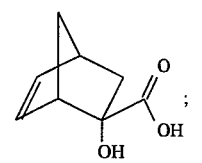
(4b)

c) subjecting the compound of Formula (4a) or (4b) obtained in the step b), to catalytic hydrogenation to form a compound represented by the Formula (5a) or (5b):

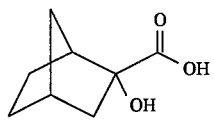
(5a)

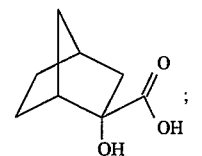
(5b)

d) subjecting the compound of Formula (5a) or (5b) obtained in the step c), to oxidative decarboxylation with a hypohalogenite to form the optically active 2-norbornanone of Formula (1a) or (1b).

2. The process according to claim 1, wherein said hypohalogenite is sodium hypochlorite.

3. A process for producing an optically active 2-hydroxynorbornene- 2-carboxylic acid represented by Formula (4a) or (4b ):

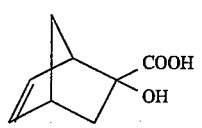
(4a)

(4b)

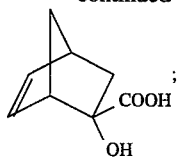

said process comprising the steps of;
a. allowing an optically active dioxolan-4-one derivative represented by Formula (2*)

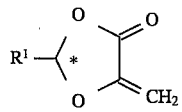
(2*)

wherein R represents a substituted or unsubstituted alkyl group or aryl group, and * represents an asymmetric carbon atom;
to react with cyclopentadiene to form a compound represented by Formula (3a) or (3b):

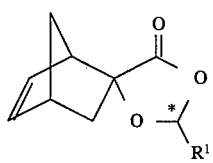
(3a)

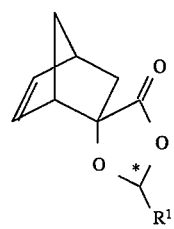
(3b)

wherein R and * are as defined in Formula (2*);
b. hydrolyzing the compound of Formula (3a) or (3b) obtained in the step a., to convert it into the optically active 2-hydroxynorbornene-2-carboxylic acid of Formula (4a) or (4b).

4. A process for producing 2-norbornanone represented by Formula (1):

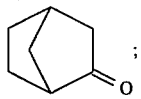
(1)

said process comprising the step of subjecting 2-hydroxynorbornane-2-carboxylic acid represented by Formula (5):

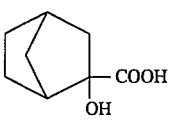
(5)

to oxidative decarboxylation in the presence of a hypohalogenite to obtain the 2-norbornanone of Formula (1).

5. The process according to claim 4, wherein said hypohalogenite is sodium hypochlorite.

6. A process for producing a 5-methylene-1,3-dioxolan-4-one represented by Formula (2):

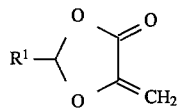
(2)

wherein $R^1$ represents a substituted or unsubstituted alkyl group or aryl group;

said process comprising the step of allowing a 5-halogeno- 5-methyl-1,3-dioxolan-4-one derivative represented by Formula (6):

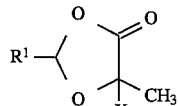
(6)

wherein $R^1$ is as defined in Formula (2), and X represents a halogen atom;
to react with a tertiary amine represented by Formula (7):

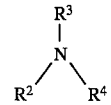
(7)

wherein $R^2$ $R^3$ and $R^4$ each independently represent an alkyl group having 4 to 12 carbon atoms;
to convert said derivative into the compound of Formula (2).

7. The process according to claim 6, wherein $R^2$, $R^3$ and $R^4$ each independently represent an alkyl group having 8 to 10 carbon atoms.

* * * * *